United States Patent
Yang et al.

(10) Patent No.: US 9,658,186 B2
(45) Date of Patent: May 23, 2017

(54) DEVICE INCLUDING VERTICALLY ALIGNED TWO-DIMENSIONAL MATERIAL

(71) Applicant: Samsung Electronics Co., Ltd., Suwon-si, Gyeonggi-do (KR)

(72) Inventors: Kiyeon Yang, Seongnam-si (KR); Changseung Lee, Yongin-si (KR); Namjeong Kim, Gwangju-si (KR); Yeonhee Kim, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/972,873

(22) Filed: Dec. 17, 2015

(65) Prior Publication Data
US 2017/0003248 A1    Jan. 5, 2017

(30) Foreign Application Priority Data

Jul. 3, 2015 (KR) .................. 10-2015-0095361

(51) Int. Cl.
*H01L 29/00* (2006.01)
*G01N 27/414* (2006.01)
*H01L 21/02* (2006.01)
*H01L 21/3065* (2006.01)
*H01L 29/786* (2006.01)

(52) U.S. Cl.
CPC ..... *G01N 27/4141* (2013.01); *H01L 21/0262* (2013.01); *H01L 21/02568* (2013.01); *H01L 21/3065* (2013.01); *H01L 29/78681* (2013.01); *H01L 29/78696* (2013.01)

(58) Field of Classification Search
CPC ............. H01L 29/78696; H01L 29/78; H01L 29/7786; G01N 27/4141
See application file for complete search history.

(56) References Cited

U.S. PATENT DOCUMENTS 7,132,678 B2   11/2006 Kagan et al.
7,202,494 B2   4/2007 Blanchard et al.
(Continued)

FOREIGN PATENT DOCUMENTS

| JP | 2014-225679 A | 12/2014 |
| KR | 101225086 B1 | 1/2013 |
| KR | 101367989 B1 | 2/2014 |

OTHER PUBLICATIONS

Wang et al., "Electronics and optoelectronics of two-dimensional transition metal dichalgenides", 2012, Nature Nanotechnology, vol. 7 pp. 699-712, published Nov. 2012.*
(Continued)

*Primary Examiner* — Nikolay Yushin
(74) *Attorney, Agent, or Firm* — Harness, Dickey & Pierce, P.L.C.

(57) ABSTRACT

A transistor includes a substrate, a two-dimensional material including at least one layer that is substantially vertically aligned on the substrate such that an edge of the layer is on the substrate and the layer extends substantially vertical to the substrate, a source electrode and a drain electrode connected to opposite ends of the two-dimensional material, a gate insulation layer on the two-dimensional material between the source electrode and the drain electrode, and a gate electrode on the gate insulation layer. Each layer includes a semiconductor having a two-dimensional crystal structure.

10 Claims, 17 Drawing Sheets

(56) References Cited

U.S. PATENT DOCUMENTS

| 8,562,874 | B2 | 10/2013 | Chow et al. | |
|---|---|---|---|---|
| 8,796,085 | B2* | 8/2014 | Koldiaev | H01L 21/845 |
| | | | | 438/212 |
| 2010/0109086 | A1 | 5/2010 | Song et al. | |
| 2014/0252315 | A1 | 9/2014 | Kim et al. | |
| 2015/0318401 | A1* | 11/2015 | Duan | H01L 29/66742 |
| | | | | 250/200 |

OTHER PUBLICATIONS

"Superlattice". Wikipedia, the free encyclopedia. Aug. 28, 2015. https://en.wikipedia.org/wiki/Superlattice.
Yeonwoong Jung et al. "Metal Seed Layer Thickness-Induced Transition From Vertical to Horizontal Growth of $MoS_2$ and $WS_2$". Nano Letters, American Chemical Society. 2014. pp. 6842-6849.
Desheng Kong et al. "Synthesis of $MoS_2$ and $MoSe_2$ Films with Vertically Aligned Layers". Nano Letters, American Chemical Society. 2013. pp. 1341-1347.
Extended European Search Report dated Dec. 12, 2016 issued in corresponding European Patent Application No. 16155085.0.
J. Noborisaka, et al. "Fabrication and characterization of freestanding GaAs/AlGaAs core-shell nanowires and AlGaAs nanotubes by using selective-area metalorganic vapor phase epitaxy," Applied Physics Letters, vol. 87. pp. 093109-1-093109-3 (2005).
Cui, et al. "Decoration of vertical graphene with aerosol nanoparticles for gas sensing," J. Phys. D. Appl. Phys. vol. 48, pp. 1-6 (2015).
Fang, et al. "Multipurpose nanoporous alumina-carbon nanowall bi-dimensional nano-hybrid platform via catalyzed and catalyst-free plasma CVD," Carbon, vol. 78, pp. 627-632 (2014).
Mao, et al. "Direct Growth of Vertically-oriented Graphene for Field-Effect Transistor Biosensor," Scientific Reports. vol. 3, No. 1696, pp. 1-6 (2013).
Kawahara, et al. "Carbon Nanowall Field Effect Transistors Using a Self-Aligned Growth Process," Journal of Surface Science and Nanotechnology, vol. 12, pp. 225-229 (2014).
Noborisaka, et al. "Catalyst-free growth of GaAs nanonwires by selective-area metalorganic vapor-phase epitaxy," Applied Physics Letters, vol. 86, pp. 213102-1-213102-3 (2005).

* cited by examiner

DEVICE INCLUDING VERTICALLY ALIGNED TWO-DIMENSIONAL MATERIAL

CROSS-REFERENCE TO RELATED APPLICATION

This application claims priority under 35 U.S.C. §119 to Korean Patent Application No. 10-2015-0095361, filed on Jul. 3, 2015, in the Korean Intellectual Property Office, the disclosure of which is incorporated herein in its entirety by reference.

BACKGROUND

1. Field

The present disclosure relates to a two-dimensional (2D) material, and more particularly, to a device including a 2D material that is vertically aligned on a substrate and/or a method of forming a 2D material that is vertically aligned on a substrate.

2. Description of Related Art

Transistors, such as semiconductor devices for performing an electrical switching function, have been used for various semiconductor products such as memory or drive integrated circuits (ICs). As the size of a semiconductor device decreases, the number of semiconductor devices obtainable from one wafer increases. Also, since a drive speed of a semiconductor device gets fast, a study to reduce the size of a semiconductor device has been actively performed.

In the case of a transistor, since a metal oxide semiconductor field effect transistor (MOSFET) having a flat structure has a limit in reducing the size thereof, a study about a fin field effect transistor (FinFET) having a three-dimensional structure has been widely performed to implement fine devices.

SUMMARY

Example embodiments relate to a two-dimensional (2D) material that is vertically aligned on a substrate and/or a method of forming a 2D material that is vertically aligned on a substrate.

Additional aspects will be set forth in part in the description which follows and, in part, will be apparent from the description, or may be learned by practice of example embodiments.

According to example embodiments, a transistor includes a substrate, a two-dimensional material including at least one layer that is substantially vertically aligned on the substrate such that an edge of the layer is on the substrate and the layer extends substantially vertical to the substrate, a source electrode and a drain electrode connected to opposite ends of the two-dimensional material, a gate insulation layer on the two-dimensional material between the source electrode and the drain electrode, and a gate electrode on the gate insulation layer. Each layer includes a semiconductor having a two-dimensional crystal structure.

In example embodiments, the two-dimensional material may include a plurality of layers that are substantially vertically aligned to the substrate. The plurality of layer may be parallel to each other.

In example embodiments, the two-dimensional material may include an upper surface and side surfaces. The gate insulation layer and the gate electrode may be on the upper surface and the side surfaces of the two-dimensional material.

In example embodiments, the two-dimensional material may include a transition metal dichalcogenide.

According to example embodiments, a gas sensor includes a substrate, at least one two-dimensional material capable of adsorbing a desired gas, the two-dimensional material including at least one layer that is substantially vertically aligned on the substrate such that an edge of the layer is on the substrate and the layer extends substantially vertical to the substrate, each layer including a semiconductor having a two-dimensional crystal structure, and first and second electrodes connected to opposite ends of the two-dimensional material.

In example embodiments, the gas sensor may further include a heater contacting the substrate. The heater may be configured to remove the desired gas from being adsorbed onto the two-dimensional material by heating the at least one two-dimensional material.

In example embodiments, the two-dimensional material may include a plurality of layers that are substantially vertically aligned to the substrate. The plurality of layer may be parallel to each other.

In example embodiments, the two-dimensional material may include a transition metal dichalcogenide.

According to example embodiments, a method of forming a two-dimensional material includes forming a guide pattern layer on a substrate, the guide pattern layer including a trench that exposes a transition metal layer on the substrate, and growing the two-dimensional material on the substrate from a portion of the transition metal layer that is exposed through the trench. The growing the two-dimensional material may include using a chemical vapor deposition method.

In example embodiments, the two-dimensional material may include at least one layer that is substantially vertically aligned on the substrate such that an edge of the layer is on the substrate and the layer extends substantially vertical to the substrate. Each layer may include a semiconductor having a two-dimensional crystal structure.

In example embodiments, the two-dimensional material may include a plurality of layers that are substantially vertically aligned to the substrate. The plurality of layers may be parallel to each other.

In example embodiments, the forming the guide pattern layer may include depositing the transition metal layer on the substrate, forming the guide pattern layer on the transition metal layer, and forming the trench in the guide pattern layer. The trench may expose the portion of the transition metal layer.

In example embodiments, the forming the guide pattern layer may include forming the guide pattern layer on the substrate, forming the trench in the guide pattern layer so the trench exposes the substrate, and depositing the transition metal layer on a surface of the substrate exposed through the trench.

In example embodiments, the transition metal layer may have a thickness of about 3 nm to about 12 nm.

In example embodiments, the trench may have a width of about 10 nm or less.

According to example embodiments, a method of forming a two-dimensional material includes forming a guide pattern layer on a substrate, the guide pattern layer having a side surface that is substantially vertical with respect to a surface of the substrate, and growing a two-dimensional material on the side surface of the guide pattern layer.

In example embodiments, the two-dimensional material may include at least one layer that is substantially vertically aligned on the substrate. An edge of the layer may be on the substrate and the layer may extend substantially vertical to the substrate. Each layer may include a semiconductor having a two-dimensional crystal structure.

In example embodiments, the forming the two-dimensional material may include depositing a transition metal layer to cover the guide pattern layer and the substrate, etching the transition metal layer to allow the transition metal layer to remain only on a side surface of the guide pattern layer, and forming the two-dimensional material from the transition metal layer using a chemical vapor deposition method.

In example embodiments, the transition metal layer may have a thickness of less than about 3 nm.

In example embodiments, the forming the two-dimensional material may include depositing the two-dimensional material to cover the guide pattern layer and the substrate using a chemical vapor deposition method, and etching the two-dimensional material to allow the two-dimensional material to remain only on a side surface of the guide pattern layer.

According to example embodiments of inventive concepts, a device may include a substrate, a two-dimensional material on the substrate, and a first electrode and a second electrode spaced apart from each other on the substrate. The two-dimensional material may include at least one layer that has a width greater than a thickness and is arranged so the width of the layer extends substantially vertical to the substrate. Each layer includes a semiconductor having a two-dimensional crystal structure. The first and second electrodes may be connected to opposite ends of the two-dimensional material.

In example embodiments, the device may further include a gate insulation layer on the two-dimensional material between the first electrode and the second electrode, and a gate electrode on the gate insulation layer. The gate electrode may be spaced apart from the first electrode and the second electrode.

In example embodiments, the device may further include a heater connected to the substrate. The two-dimensional material may be over the heater. A gas may be capable of adsorbing to the two-dimensional layer. The heater may be configured to remove the gas from being adsorbed on the two-dimensional material by heating the two-dimensional material.

In example embodiments, the two-dimensional material may include a transition metal dichalcogenide.

In example embodiments, the two-dimensional material may include a plurality of layers that are substantially vertically aligned to the substrate. The plurality of layers may be parallel to each other.

BRIEF DESCRIPTION OF THE DRAWINGS

The foregoing and other features of inventive concepts will be apparent from the more particular description of non-limiting embodiments of inventive concepts, as illustrated in the accompanying drawings in which like reference characters refer to like parts throughout the different views. The drawings are not necessarily to scale, emphasis instead being placed upon illustrating principles of inventive concepts. In the drawings.

DETAILED DESCRIPTION

Figure 1:
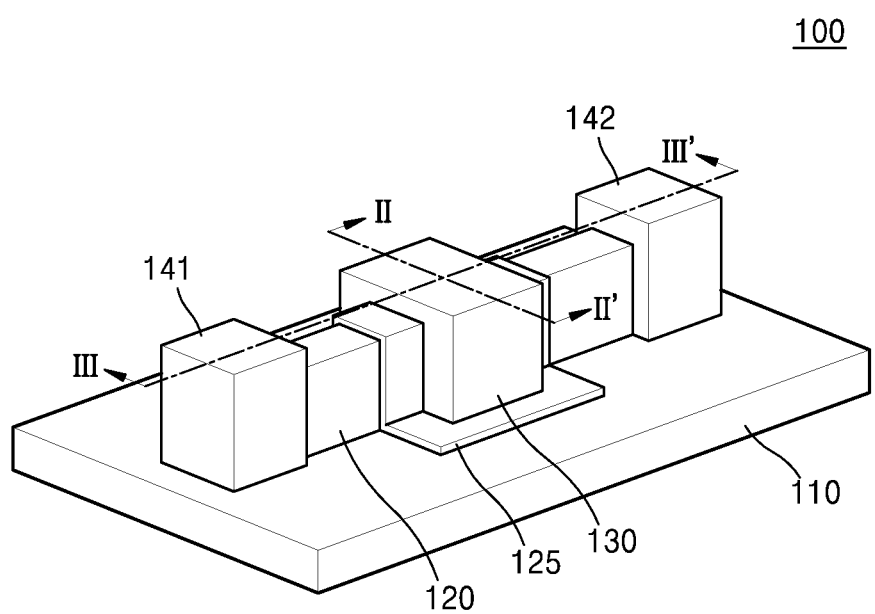
FIG. 1 is a perspective view of a transistor according to example embodiments.

Example embodiments will now be described more fully with reference to the accompanying drawings, in which some example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference characters and/or numerals in the drawings denote like elements, and thus their description may not be repeated.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on"). As used herein the term "and/or" includes any and all combinations of one or more of the associated listed items.

It will be understood that, although the terms "first", "second", etc. may be used herein to describe various elements, components, regions, layers and/or sections. These elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof. Expressions such as "at least one of," when preceding a list of elements, modify the entire list of elements and do not modify the individual elements of the list.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an etched region or an implanted region illustrated as a rectangle may have rounded or curved features. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Reference will now be made in detail to a semiconductor device including contact of metal-two dimensional material-semiconductor, examples of which are illustrated in the accompanying drawings, wherein like reference numerals refer to like elements throughout. Also, the size of each layer illustrated in the drawings may be exaggerated for convenience of explanation and clarity. In this regard, the example embodiments may have different forms and should not be construed as being limited to the descriptions set forth herein. Accordingly, example embodiments described below are merely non-limiting examples, by referring to the figures, to explain aspects of inventive concepts. In a layer structure, when a constituent element is disposed "above" or "on" to another constituent element, the constituent element may be only directly on the other constituent element or above the other constituent elements in a non-contact manner.

Figure 2:
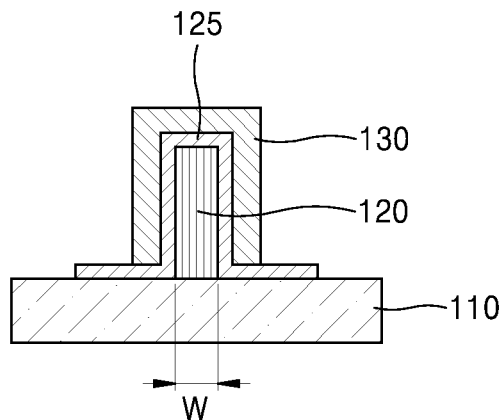
FIG. 2 is a cross-sectional view taken along a line II-II' of FIG. 1.
Figure 3:
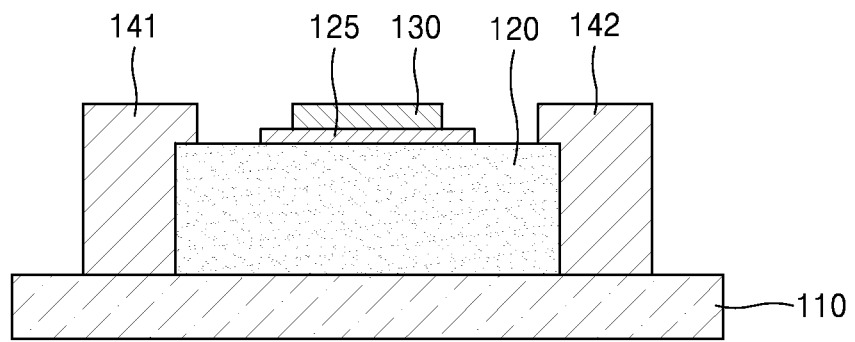
FIG. 3 is a cross-sectional view taken along a line III-III' of FIG. 1.

FIG. 1 is a perspective view of a transistor 100 according to example embodiments. FIG. 2 is a cross-sectional view taken along a line II-II' of FIG. 1. FIG. 3 is a cross-sectional view taken along a line III-III' of FIG. 1. The transistor 100 illustrated in FIGS. 1 to 3 may include a fin field effect transistor (FinFET).

Referring to FIGS. 1 to 3, the transistor 100 may include a substrate 110, a two-dimensional (2D) material 120 provided on the substrate 110, the source and drain electrodes 141 and 142 provided at opposite sides of the 2D material 120, and a gate insulation layer 125 and a gate electrode 130 that are sequentially formed on the 2D material 120.

The substrate 110 may be a semiconductor substrate on which an insulating material is formed. For example, the substrate 110 may be a silicon substrate on which an oxide layer is formed. However, the example embodiments are not limited thereto and substrates of various materials may be used therefor. The 2D material 120 used as a channel material may be provided on an upper surface of the substrate 110. The 2D material 120' denotes a semiconductor material having a crystal structure of a 2D shape and may have a monolayer or multilayer structure. Each layer forming the 2D material may have a thickness of an atomic level. The layers forming the 2D material 120 may be connected by the Van Der Waals bond.

In example embodiments, the respective layers forming the 2D material 120 are substantially vertically aligned with respect to the substrate 110. In other words, as shown in FIG. 2, each layer of the 2D material 120 may have a width that is greater than its thickness. In order to be substantially vertically aligned with respect to the substrate 110, the edges of a layer may be defined by the thickness of the layer and the edges of the layer may be on the substrate 110 while the layer extends in the width direction perpendicular to the substrate. The term "substantially vertically" denotes being "exactly vertically" or "almost vertically". The 2D material 120 may have a width W, for example, about 10 nm or less (e.g., greater than 0 nm and less than equal to about 10 nm). However, the present disclose is not limited thereto. Also, the number of layers forming the 2D material 120 may be about one or a few. For example, the number of layers forming the 2D material 120 may in a range of one to ten and/or one to five. However, this is merely a non-limiting example and the 2D material 120 may include more layers than the above. Also, when the 2D material 120 includes a plurality of layers, the layers may be arranged parallel to each other with directivity.

The 2D material 120 is a material that may be applied to various devices because it has superior electrical characteristics and can maintain high mobility without much change in its characteristics even when the thickness decrease to a nano scale. For example, the 2D material 120 may include transition metal dichalcogenide (TMD). TMD is a semiconductor material having a 2D crystal structure and may include, for example, one of transition metals of Mo, W, Nb, V, Ta, Ti, Zr, Hf, Tc, and Re and one of chalcogen elements of S, Se, and Te. TMD may be expressed by, for example, $MX_2$, where "M" denotes a transition metal and "X" denotes a chalcogen element. For example, "M" may be Mo, W, Nb, V, Ta, Ti, Zr, Hf, Tc, or Re and "X" may be S, Se, or Te. Accordingly, for example, TMD may include $MoS_2$, $MoSe_2$, $MoTe_2$, $WS_2$, $WSe_2$, $WTe_2$, $ZrS_2$, $ZrSe_2$, $HfS_2$, $HfSe_2$, $NbSe_2$, or $ReSe_2$. Alternatively, TMD may not be expressed by $MX_2$. In this case, for example, TMD includes CuS that is a compound of a transition metal of Cu and a chalcogen element of S. Alternatively, TMD may be a chalcogenide material including a non-transition metal. The non-transition metal may include, for example, Ga, In, Sn, Ge, or Pb. In this case, TMD may include a compound of a non-transition metal such as Ga, In, Sn, Ge, or Pb and a chalcogen element such as S, Se, or Te. For example, TMD may include $SnSe_2$, GaS, GaSe, GaTe, GeSe, $In_2Se_3$, or $InSnS_2$.

To summarize the above, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, the above-described materials are mere a non-limiting example and other material may be used as a TMD material.

The 2D material 120 may be doped with a p-type dopant or an n-type dopant to control mobility. A p-type dopant and an n-type dopant used for graphene or carbon nanotube (CNT), for example, may be used as the p-type dopant and the n-type dopant. The p-type dopant or the n-type dopant may be doped by an ion implantation method or a chemical doping method.

A source of the p-type dopant may include, for example, ionic liquid such as $NO_2BF_4$, $NOBF_4$, or $NO_2SbF_6$, acidic compound such as HCl, $H_2PO_4$, $CH_3COOH$, $H_2SO_4$, or $HNO_3$, or organic compound such as dichlorodicyanoquinone (DDQ), oxone, dimyristoylphosphatidylinositol (DMPI), or trifluoromethanesulfoneimide. Alternatively, a source of the p-type dopant may include $HPtCl_4$, $AuCl_3$, $HAuCl_4$, silver trifluoromethanesulfonate (AgOTf), $AgNO_3$, $H_2PdCl_6$, $Pd(OAc)_2$, or $Cu(CN)_2$.

A source of the n-type dopant may include, for example, a reduction product of a substituted or unsubstituted nicotinamide; a reduction product of a compound which is chemically bound to a substituted or unsubstituted nicotinamide, and a compound comprising at least two pyridinium moieties in which a nitrogen atom of at least one of the pyridinium moieties is reduced. For example, a source of the n-type dopant may include nicotinamide mononucleotide-H (NMNH), nicotinamide adenine dinucleotide-H (NADH), nicotinamide adenine dinucleotide phosphate-H (NADPH), or viologen. Also, a source of the n-type dopant may include polymer such as polyethylenimine (PEI). Also, the n-type dopant may include an alkali metal such as K or Li. Alternatively, the above-described p-type dopant and n-type dopant materials are a non-limiting example and other various materials may be used as dopants.

The source and drain electrodes 141 and 142 are provided on the substrate 110. The source and drain electrodes 141 and 142 may be electrically connected to opposite ends of the 2D material 120. The source and drain electrodes 141 and 142 may include metal materials exhibiting superior electrical conductivity, for example, Ag, Au, Pt, or Cu. However, example embodiments are not limited thereto.

The gate insulation layer 125 is provided on the 2D material 120 between the source electrode 141 and the drain electrode 142. The gate insulation layer 125 may cover an upper surface and side surfaces of the 2D material 120. The gate insulation layer 125 may include, for example, a silicon oxide, a silicon nitride, an aluminum oxide, a hafnium oxide, or an insulating polymer. However, this is a non-limiting example and the gate insulation layer 125 may include various insulation materials.

The gate electrode 130 is provided on the gate insulation layer 125. The gate electrode 130 may be provided corresponding to the upper surface and side surfaces of the 2D material 120. Like the source and drain electrodes 141 and 142, the gate electrode 130 may include a metal material exhibiting superior electrical conductivity, for example, Ag, Au, Pt, or Cu. However, example embodiments are not limited thereto.

In the case of a Si-based FinFET, when the thickness of silicon is reduced to several nanometers or less, the number of carriers in silicon decreases and accordingly electron mobility decreases as well. However, in example embodiments, the 2D material 120 employed as a channel material may maintain high electron mobility even when the thickness is reduced to several nanometers or less. Also, when the source and drain electrodes 141 and 142 formed of metal are in contact parallel with a layer on a surface of the 2D material 120, a contact resistance between the metal and the 2D material 120 increases due to an increase in a contact area. In example embodiments, however, as layers forming the 2D material 120 vertically contact the source and drain electrodes 141 and 142 formed of metal, the contact resistance between the metal and the 2D material 120 may be reduced. Also, when only the layer on the surface of the 2D material 120 is in contact with the source and drain electrodes 141 and 142, series resistance between the layers of the 2D material 120 greatly increases. In example embodiments, however, since all layers forming the 2D material 120 are in contact with the source and drain electrodes 141 and 142, the series resistance generated between the layers of the 2D material 120 may be reduced.

As described above, in example embodiments, a transistor of a fine size with superior performance, for example, a FinFET having a fine channel width of about 10 nm or less, may be implemented by aligning the 2D material 120 used as a channel material vertically with the substrate 110 and arranging the layers forming the 2D material 120 with a desired (and/or alternatively predetermined) directivity and in parallel to each other.

FIGS. 4A to 4D illustrate a method of forming a 2D material according to example embodiments.

Figure 4A:
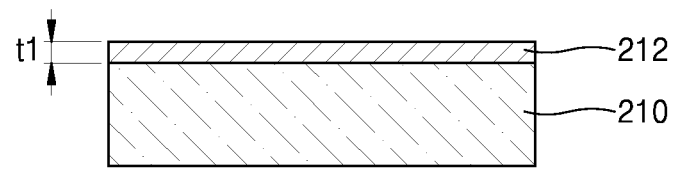
FIGS. 4A to 4D illustrate a method of forming a two-dimensional (2D) material according to example embodiments.

Referring to FIG. 4A, after a substrate 210 is prepared, a transition metal layer 212 is deposited on the substrate 210 to a desired (and/or alternatively predetermined) thickness t1. The transition metal layer 212 may be deposited to a particular thickness or more to allow a 2D material (220 in FIG. 4D) to vertically grow from the substrate 210, as described below. Meanwhile, when the transition metal layer 212 has a thickness less than the particular thickness, a 2D material aligned parallel to the substrate 210 may be formed. In example embodiments, the transition metal layer 212 may have the thickness t1 of about 3 nm to about 12 nm to form the 2D material 220 that is vertically aligned on the substrate 210. However, example embodiments are not limited thereto.

Figure 4B:
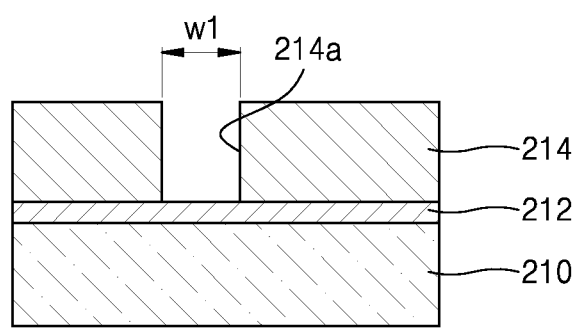

Referring to FIG. 4B, a guide pattern layer 214 including a trench 214A (e.g., opening) is formed in the transition metal layer 212. First, a guide pattern layer 214 covers the transition metal layer 212. The guide pattern layer 214 may include a material having no reactivity to the transition metal layer 212, for example, an insulation material. Next, a trench 214A that exposes the transition metal layer 212 has a desired (and/or alternatively predetermined) width W1 by patterning the guide pattern layer 214 in a desired (and/or alternatively predetermined) shape. The trench 214A formed in the guide pattern layer 214 may guide a plurality of layers forming the 2D material 220 of FIG. 4D to be described later, to grow with a desired (and/or alternatively predetermined) directivity and in parallel to each other. The width W1 of the trench 214A may be equal to or less than about 10 nm. However, example embodiments are not limited thereto.

Figure 4C:
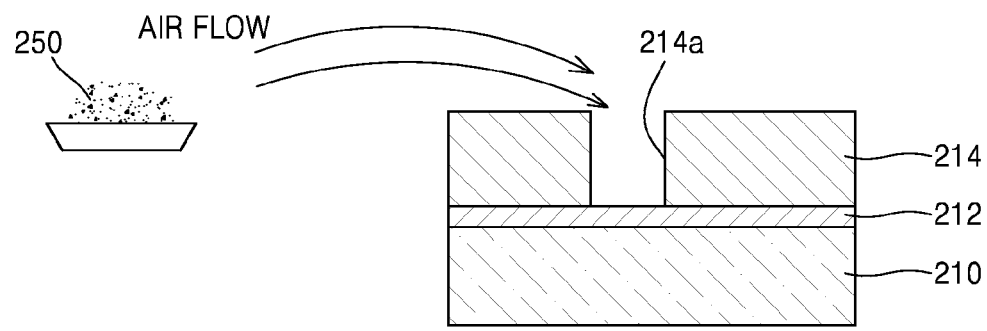
Figure 4D:
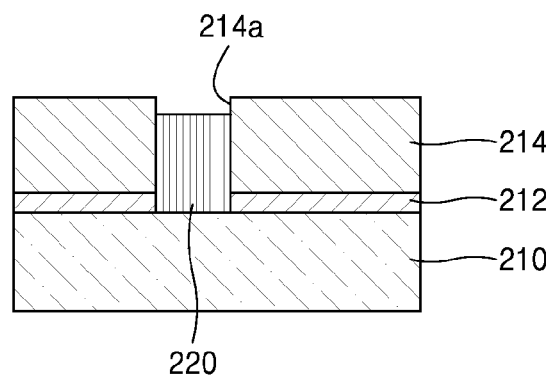

Referring to FIGS. 4C and 4D, the 2D material 220 that is vertically aligned with the substrate 210 is formed within the trench 214A from the transition metal layer 212 that is exposed through the trench 214A. The 2D material 220 may include a plurality of layers that are vertically aligned with respect to the substrate 210 and the layers may be formed with directivity and in parallel to each other.

As described above, the 2D material 220 may denote a semiconductor material having a 2D crystal structure. The 2D material 220 may include TMD. For example, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, the above-described materials are merely non-limiting examples and other materials may be used for TMD. Meanwhile, the 2D material 220 may be doped with impurities. For example, the 2D material 220 may be doped with a p-type dopant or an n-type dopant. A p-type dopant and an n-type dopant used for graphene or carbon nanotube (CNT), for example, may be used as the p-type dopant and the n-type dopant.

The 2D material 220 may be formed by a chemical vapor deposition (CVD) method, in detail, a thermal CVD method. The thermal CVD method of forming the 2D material 220 that is vertically aligned on the substrate 210 is described below. In the following description, a case of forming a $MoS_2$ 2D material 220 that is vertically aligned on the substrate 210 from a Mo transition metal layer 212 is described as an example.

First, referring to FIG. 4C, a structure illustrated in FIG. 4B and sulfur powder 250 are provided within a tube furnace (not shown). Next, when the sulfur powder 250 is heated to a desired (and/or alternatively predetermined) temperature, for example, about 600° C. to about 1000° C., the sulfur powder 250 is vaporized and sulfur vapor is moved along a flow of an inert gas, for example, Ar, into the trench 214A. Next, the sulfur stream flowing into the trench 214A generates sulfurization by contacting the Mo transition metal layer 212 and thus, as illustrated in FIG. 4D, the $MoS_2$ 2D material 220 grows within the trench 214A. When the sulfur powder 250 is heated, a process temperature of the tube furnace (not shown) may be about 600° C. to about 1000° C.

In the growth of the $MoS_2$ 2D material 220, as described above, since the Mo transition metal layer 212 is deposited to the desired (and/or alternatively predetermined) thickness t1, the $MoS_2$ 2D material 220 including a plurality of layers vertically aligned with respect to the substrate 210 may be formed in the trench 214A. Also, the layers forming the MoS2 2D material 220 may be formed with a desired (and/or alternatively predetermined) directivity and in parallel to each other by the trench 214A formed in the guide pattern layer 214. The 2D material 220 vertically aligned in the trench 214A may have a height roughly twice the thickness t1 of the transition metal layer 212, but example embodiments are not limited thereto.

Meanwhile, as illustrated in FIG. 4D, after the 2D material 220 is formed on the substrate 210 within the trench 214A, the transition metal layer 212 and the guide pattern layer 214 around the 2D material 220 may be removed. Accordingly, only the 2D material 220 that is vertically aligned may be left on the substrate 210.

FIGS. 5A to 5D illustrate a method of forming a 2D material according to example embodiments.

Figure 5A:
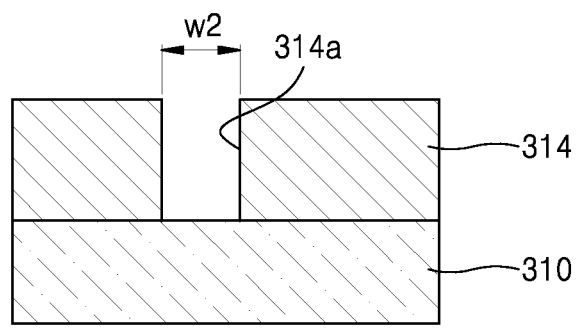
FIGS. 5A to 5D illustrate a method of forming a 2D material according to example embodiments.

Referring to FIG. 5A, after a substrate 310 is prepared, a guide pattern layer 314 including a trench 314A (e.g., opening) is formed on the substrate 310. First, the guide pattern layer 314 covers the substrate 310. The guide pattern layer 314 may include, for example, an insulation material.

Next, the trench 314A that exposes the substrate 310 has a desired (and/or alternatively predetermined) width W2 by patterning the guide pattern layer 314. The trench 314A formed in the guide pattern layer 314 may guide a plurality of layers forming a 2D material 320 of FIG. 5D to be described layer, to be formed with a desired (and/or alternatively predetermined) directivity and in parallel to each other. For example, the trench 314A may have the width of about 10 nm or less. However, example embodiments are not limited thereto.

Figure 5B:
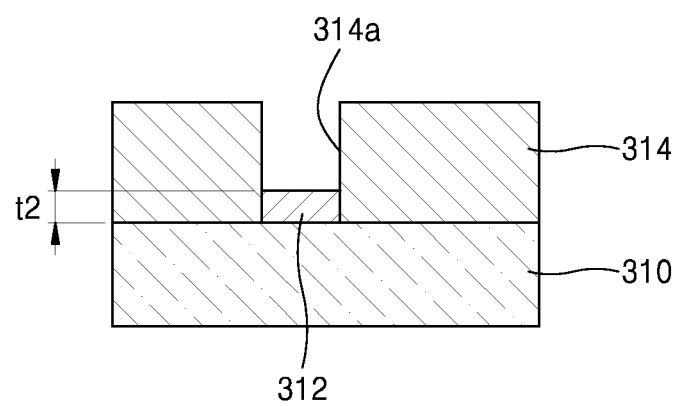

Referring to FIG. 5B, a transition metal layer 312 is deposited on the substrate 310 that is exposed through the trench 314A. The transition metal layer 312 formed in the trench 314A may be deposited to a desired (and/or alternatively predetermined) thickness t2 to grow the 2D material 320 vertically with respect to the substrate 310, as described below. For example, the transition metal layer 312 may be deposited to a thickness t2 of about 3 nm to about 12 nm. However, example embodiments are not limited thereto. The deposited transition metal layer 312 may be exposed through the trench 314A.

Figure 5C:
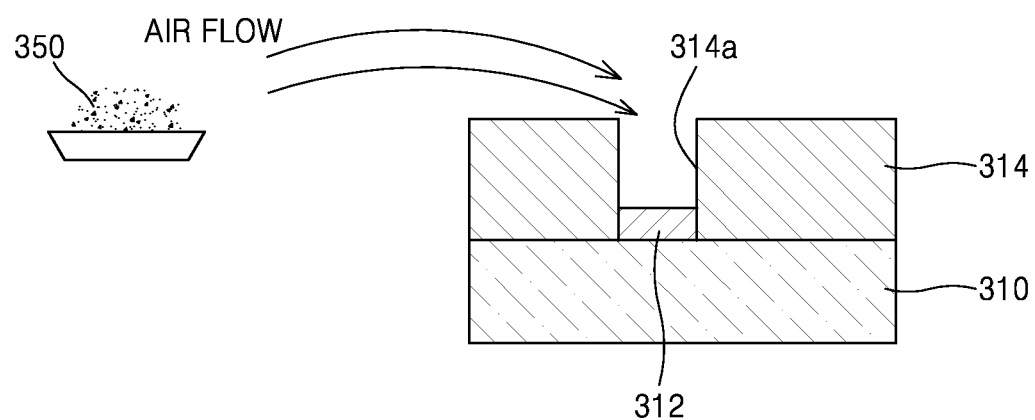
Figure 5D:
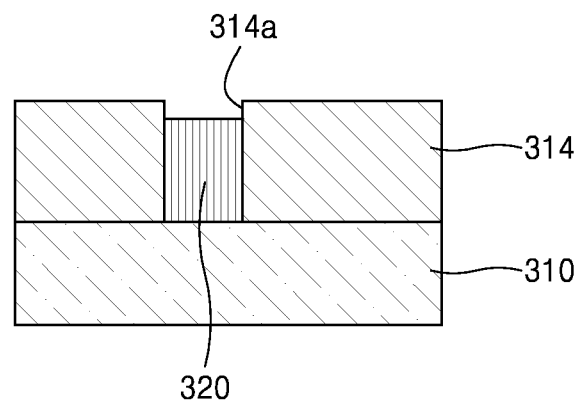

Referring to FIGS. 5C and 5D, the 2D material 320 that is vertically aligned with respect to the substrate 310 within the trench 314A is formed from the transition metal layer 312 that is exposed through the trench 314A. The 2D material 320 may include a plurality of layers that are vertically aligned with respect to the substrate 310, and the layers may be formed with a desired (and/or alternatively predetermined) directivity and in parallel to each other.

As described above, the 2D material 320 may include TMD. For example, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, example embodiments are not limited thereto. Meanwhile, the 2D material 320 may be doped with impurities.

The 2D material 320 may be formed by a CVD method, in detail, a thermal CVD method. A method of forming the 2D material 320 that is vertically aligned on the substrate 310 by the thermal CVD method is described below. In the following description, a case of forming a $MoS_2$ 2D material 320 that is vertically aligned on the substrate 310 from a Mo transition metal layer 312 is described as an example.

First, referring to FIG. 5C, a structure illustrated in FIG. 5B and sulfur powder 350 are provided within a tube furnace (not shown). Next, when the sulfur powder 350 is heated to a desired (and/or alternatively predetermined) temperature, for example, about 600° C. to about 1000° C., the sulfur powder 350 is vaporized and sulfur vapor is moved along a flow of an inert gas (e.g., Ar) into the trench 314A. Next, the sulfur stream flowing into the trench 314A generates sulfurization by contacting the Mo transition metal layer 312 and thus, as illustrated in FIG. 5D, the $MoS_2$ 2D material 320 grows within the trench 314A. When the sulfur powder 350 is heated, a process temperature of the tube furnace (not shown) may be about 600° C. to about 1000° C.

In the growth of the $MoS_2$ 2D material 320, as described above, since the Mo transition metal layer 312 is deposited to a desired (and/or alternatively predetermined) thickness t2, the MoS2 2D material 320 growing within the trench 314A may include a plurality of layers vertically aligned with respect to the substrate 310. Also, the layers forming the MoS2 2D material 320 may be formed with a desired (and/or alternatively predetermined) directivity and in parallel to each other by the trench 314A formed in the guide pattern layer 314. The 2D material 320 vertically aligned in the trench 314A may have a height roughly twice a thickness of the transition metal layer 312, but example embodiments are not limited thereto.

Meanwhile, as illustrated in FIG. 5D, after the 2D material 320 that is vertically aligned within the trench 314A is formed, the guide pattern layer 314 around the 2D material 320 may be removed. Accordingly, only the 2D material 320 that is vertically aligned may be left on the substrate 310.

Figure 6A:
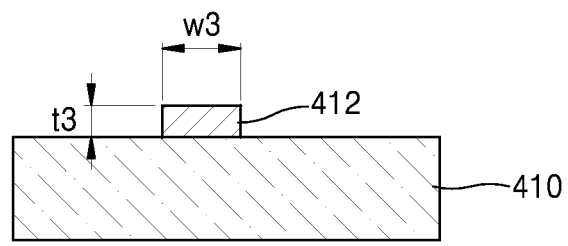
FIGS. 6A to 6C illustrate a method of forming a 2D material according to example embodiments.
Figure 6B:
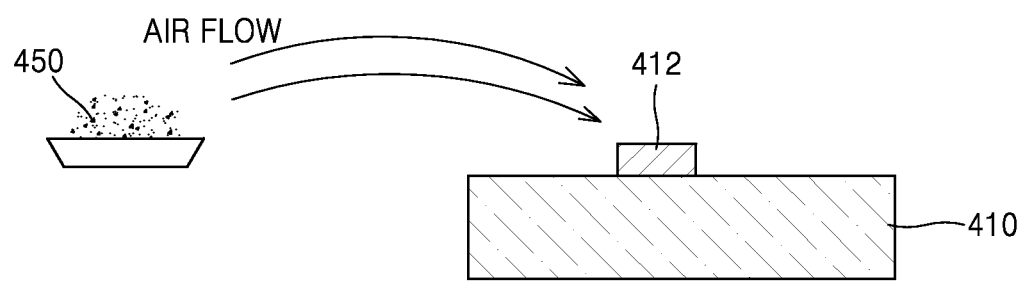
Figure 6C:
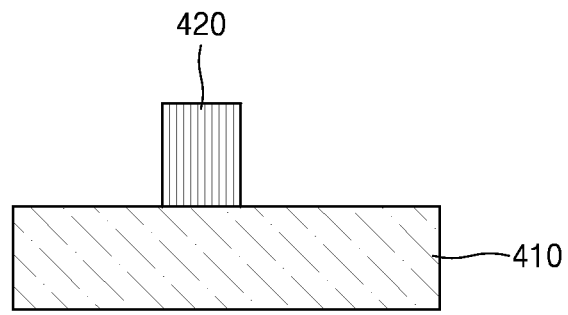

FIGS. 6A to 6C illustrate a method of forming a 2D material according to example embodiments.

Referring to FIG. 6A, after a substrate 410 is prepared, a transition metal layer 412 having a desired (and/or alternatively predetermined) width W3 and a desired (and/or alternatively predetermined) thickness t3 is formed on the substrate 410. The transition metal layer 412 may be formed as follows. First, the transition metal layer 412 is deposited to cover the substrate 410. The transition metal layer 412 may be deposited to the desired (and/or alternatively predetermined) thickness t3, to grow a 2D material 420 to be described later to be vertically on the substrate 410. For example, the transition metal layer 412 may be deposited to the desired (and/or alternatively predetermined) thickness t3 of about 3 nm to about 12 nm. However, example embodiments are not limited thereto. Next, the transition metal layer 412 having a desired (and/or alternatively predetermined) width W3 is formed on the substrate 410 through a patterning process. The transition metal layer 412 may have a width W3 of, for example, about 10 nm or less, but example embodiments are not limited thereto.

Referring to FIGS. 6B and 6C, the 2D material 420 that is vertically aligned on the substrate 410 is formed from the transition metal layer 412 having the desired (and/or alternatively predetermined) width W3 and the desired (and/or alternatively predetermined) thickness t3 that is formed on the substrate 410. The 2D material 420 may include a plurality of layers that are vertically aligned with respect to the substrate 410, and the layers may be formed with a desired (and/or alternatively predetermined) directivity and in parallel to each other As described above, the 2D material 420 may include TMD. For example, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, example embodiments are not limited thereto. Alternatively, the 2D material 420 may be doped with impurities.

The 2D material 420 may be formed by a CVD method, in detail, a thermal CVD method. A method of forming the 2D material 420 that is vertically aligned on the substrate 410 by the thermal CVD method is described below. In the following description, a case of forming a $MoS_2$ 2D material 420 that is vertically aligned on the substrate 410 from a Mo transition metal layer 412 is described as an example.

First, referring to FIG. 6B, a structure illustrated in FIG. 6A and sulfur powder 450 are provided within a tube furnace (not shown). Next, when the sulfur powder 450 is heated to a desired (and/or alternatively predetermined) temperature, for example, about 600° C. to about 1000° C., the sulfur powder 450 is vaporized and sulfur vapor is moved along a flow of an inert gas, for example, Ar, to contact the Mo transition metal layer 412 generating sulfurization. Accordingly, as illustrated in FIG. 6C, the $MoS_2$ 2D material 420 grows. When the sulfur powder 450 is heated, a process temperature of the tube furnace (not shown) may be about 600° C. to about 1000° C.

In the growth of the $MoS_2$ 2D material 420, since the Mo transition metal layer 412 is deposited to the desired (and/or alternatively predetermined) thickness t3, the $MoS_2$ 2D material 420 may include a plurality of layers vertically aligned with respect to the substrate 410. Also, since the transition metal layer 412 has the desired (and/or alternatively predetermined) width W3, for example, about 10 nm or less, the layers forming the $MoS_2$ 2D material 420 may be formed with a desired (and/or alternatively predetermined) directivity and in parallel to each other.

Figure 7A:
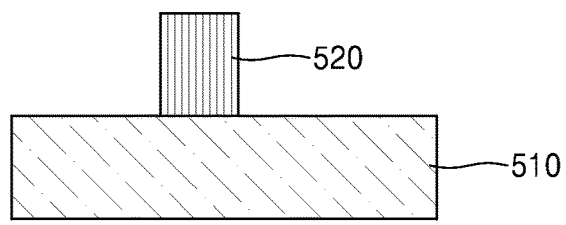
FIGS. 7A to 7C illustrate a method of manufacturing a transistor according to example embodiments.
Figure 7B:
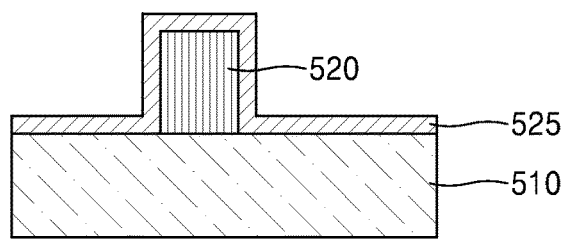
Figure 7C:
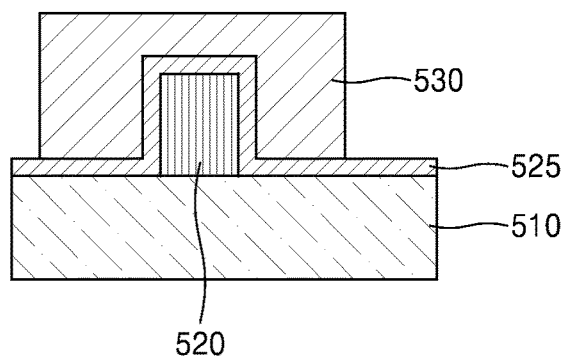

FIGS. 7A to 7C illustrate a method of manufacturing a transistor according to example embodiments.

Referring to FIG. 7A, a 2D material 520 that is vertically aligned is formed on a substrate 510. A silicon substrate, on which an oxide layer is formed, for example, may be used as the substrate 510. However, example embodiments are not limited thereto and a substrate formed of other various materials may be used therefor. The 2D material 520 including at least one layer that is vertically aligned with respect to the substrate 510 is provided on an upper surface of the substrate 510. Since the 2D material 520 is described above, a detailed description thereof is omitted.

Referring to FIG. 7B, a gate insulation layer 525 is deposited on the substrate 510 and the 2D material 520. The gate insulation layer 525 may cover an upper surface and side surfaces of the 2D material 520. The gate insulation layer 525 may include, for example, a silicon oxide, a silicon nitride, an aluminum oxide, a hafnium oxide, or an insulating polymer. However, this is merely exemplary and the gate insulation layer 525 may include various insulation materials.

Referring to FIG. 7C, a gate electrode 530 is deposited on the gate insulation layer 525. The gate electrode 530 may be provided corresponding to upper surface and side surfaces of the 2D material 520. The gate electrode 530 may include a metal material exhibiting superior electrical conductivity, for example, Ag, Au, Pt, or Cu. However, example embodiments are not limited thereto.

Although not illustrated, a source electrode and a drain electrode are formed at opposite ends of the 2D material 520. The source electrode and the drain electrode may be simultaneously formed with the gate electrode 530.

FIGS. 8A to 8D illustrate a method of forming a 2D material according to example embodiments.

Figure 8A:
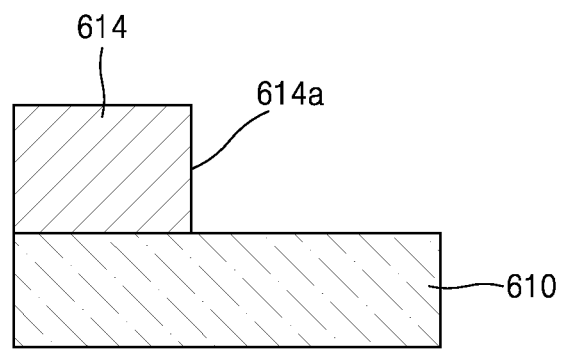
FIGS. 8A to 8D illustrate a method of forming a 2D material according to example embodiments.
Figure 8B:
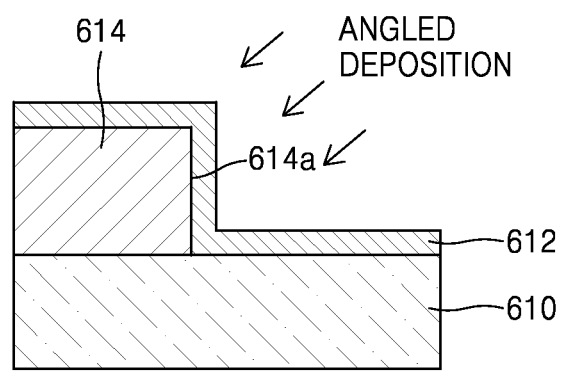

Referring to FIG. 8A, first, after a substrate 610 is prepared, a guide pattern layer 614 that exposes a surface of the substrate 610 is formed on the substrate 610. The guide pattern layer 614 includes a side surface 614A that is substantially vertical with respect to the surface of the substrate 610. Referring to FIG. 8B, a transition metal layer 612 is deposited to cover the substrate 610 and the guide pattern layer 614. In this case, angled deposition may be performed on the side surface 614A of the guide pattern layer 614 to facilitate deposition of the transition metal layer 612.

Figure 8C:
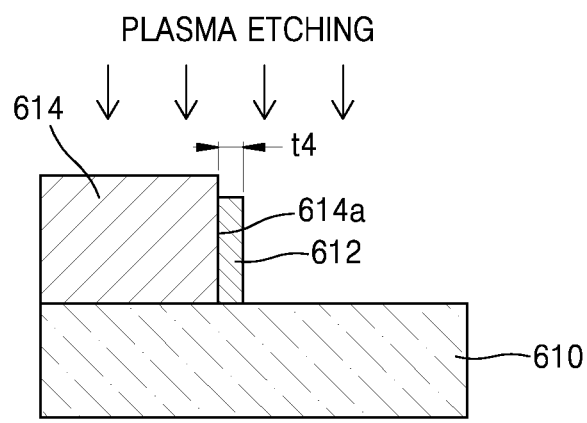

Referring to FIG. 8C, the transition metal layer 612 formed on an upper surface of the guide pattern layer 614 and an upper surface of the substrate 610 are removed by etching so that the transition metal layer 612 may remain only on the side surface 614A of the guide pattern layer 614. In this case, the transition metal layer 612 may be etched by, for example, plasma, but not limited thereto. As such, the transition metal layer 612 remaining on the side surface 614A of the guide pattern layer 614 through etching may have a desired (and/or alternatively predetermined) thickness t4. The transition metal layer 612 may have the desired (and/or alternatively predetermined) thickness t4 that is less than a specific thickness of the side surface 614A of the guide pattern layer 614. The transition metal layer 612 may have the desired (and/or alternatively predetermined) thickness t4 that is less than, for example, about 3 nm. However, example embodiments are not limited thereto. As such, when the transition metal layer 612 has the desired (and/or alternatively predetermined) thickness t4 that is less than a specific thickness, as described below, a 2D material that is aligned in parallel to the side surface 614A of the guide pattern layer 614 may be formed from the transition metal layer 612. Accordingly, a 2D material 620 that is aligned substantially vertically may be formed on the substrate 610.

Figure 8D:
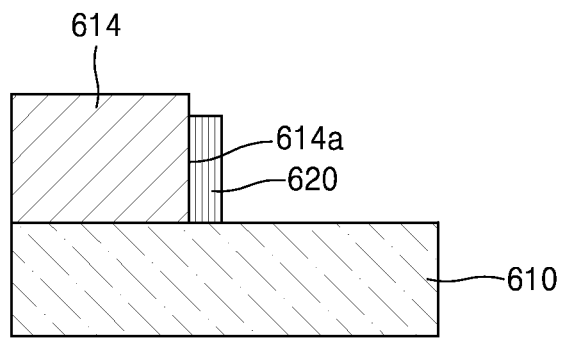

Referring to FIG. 8D, the 2D material 620 is grown from the transition metal layer 612 by a CVD method, in detail, a thermal CVD method. Since the transition metal layer 612 has the desired (and/or alternatively predetermined) thickness t4, for example, less than 3 nm, the 2D material 620 formed from the transition metal layer 612 may grow to be substantially parallel to the side surface 614A of the guide pattern layer 614, that is, substantially vertically with respect to the substrate 610. The 2D material 620 may include a monolayer or a few layers. As described above, the 2D material 620 may include TMD. For example, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, example embodiments are not limited thereto. Meanwhile, the 2D material 620 may be doped with impurities.

As illustrated in FIG. 8D, after the 2D material 620 that is vertically aligned on the substrate 610 is formed, the guide pattern layer 614 remaining around the 2D material 620 may be removed. Accordingly, only the 2D material 620 that is vertically aligned may be left on the substrate 610.

Figure 9A:
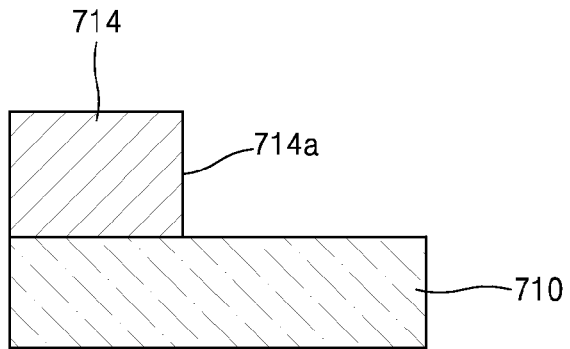
FIGS. 9A to 9C illustrate a method of forming a 2D material according to example embodiments.
Figure 9B:
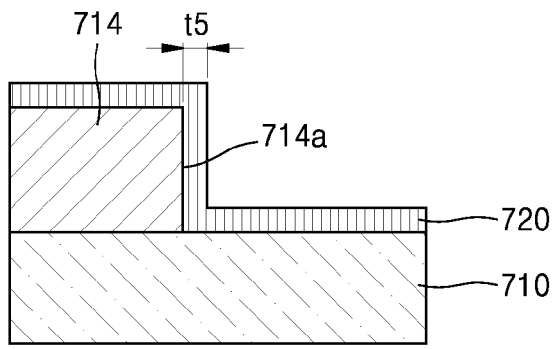
Figure 9C:
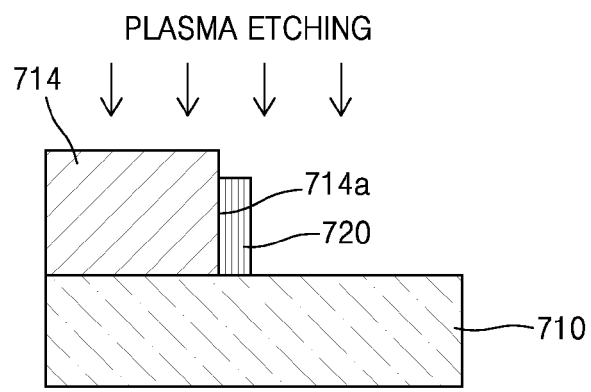

FIGS. 9A to 9C illustrate a method of forming a 2D material according to example embodiments.

Referring to FIG. 9A, first, after a substrate 710 is prepared, a guide pattern layer 714 that exposes a surface of the substrate 710 is formed on the substrate 710. The guide pattern layer 714 includes a side surface 714A that is substantially vertical with respect to the surface of the substrate 710.

Referring to FIG. 9B, a 2D material 720 is deposited to cover the substrate 710 and the guide pattern layer 714. The 2D material 720 may include a monolayer or a few layers. The 2D material 720 that is substantially vertically aligned on the substrate 710 may be formed on the side surface 714A of the guide pattern layer 714, through the deposition of the 2D material 720. In other words, in the deposition process of the 2D material 720, the respective layers forming the 2D material 720 are formed in parallel to the side surface 714A of the guide pattern layer 714. Accordingly, the 2D material 720 that is vertically formed with respect to the substrate 710 may have the desired (and/or alternatively predetermined) thickness t5 on the side surface 714A of the guide pattern layer 714. The 2D material 720 may include TMD, as described above. For example, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, example embodiments are not limited thereto. Meanwhile, the 2D material 720 may be doped with impurities.

Referring to FIG. 9C, when the 2D material 720 remaining on an upper surface of the guide pattern layer 714 and an upper surface of the substrate 710 is removed by etching. The 2D material 720 that is substantially vertically aligned with respect to the substrate 710 is left on the side surface 714A of the guide pattern layer 714. As illustrated in FIG. 9C, after the 2D material 720 that is vertically aligned on the substrate 710 is formed, the guide pattern layer 714 remaining around the 2D material 720 may be removed. Accordingly, only the 2D material 720 that is vertically aligned on the substrate 710 may remain on the substrate 710.

FIGS. 10A to 10D illustrate a method of manufacturing a transistor according to example embodiments. FIGS. 10A to 10D illustrate a method of manufacturing a transistor from the structure illustrated in FIG. 8C or FIG. 9C.

Figure 10A:
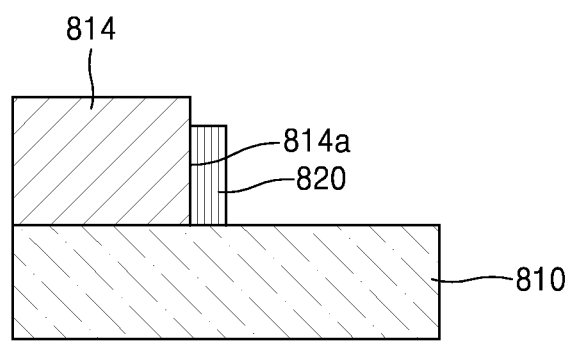
FIGS. 10A to 10D illustrate a method of manufacturing a transistor according to example embodiments.

Referring to FIG. 10A, a guide pattern layer 814 formed of an insulation material and having a side surface 814A that is substantially vertical with respect to a substrate 810 is formed on the substrate 810. A 2D material 820 is formed on the side surface 814A of the guide pattern layer 814. The 2D material 820 may include a monolayer or a few layers and the respective layers may be substantially vertically aligned on the substrate 810.

Figure 10B:
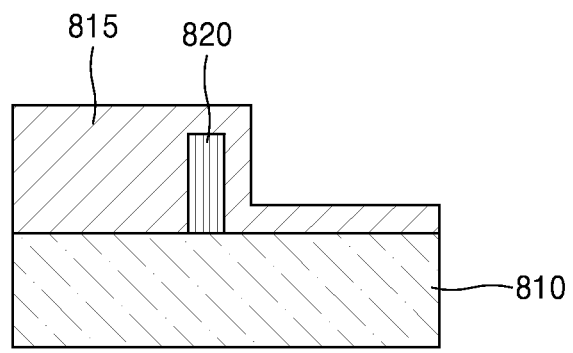
Figure 10C:
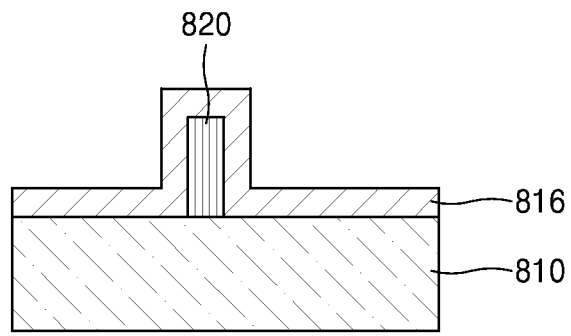

Referring to FIG. 10B, in the structure of FIG. 10A, an insulation material is deposited to cover the 2D material 820 and the substrate 810, thereby forming a dielectric layer 815. Next, as illustrated in FIG. 10C, a gate insulation layer 816 is formed by etching the dielectric layer 815.

Figure 10D:
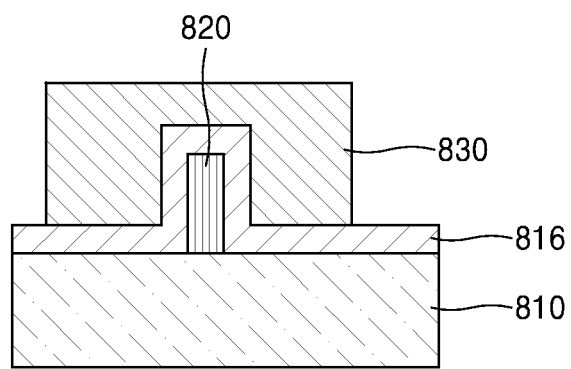

Referring to FIG. 10D, the gate electrode 830 is deposited on the gate insulation layer 816. The gate electrode 830 may be formed on an upper surface and side surfaces of the 2D material 820. The gate electrode 830 may include, for example, a metal material exhibiting superior electrical conductivity. However, example embodiments are not limited thereto.

Figure 11:
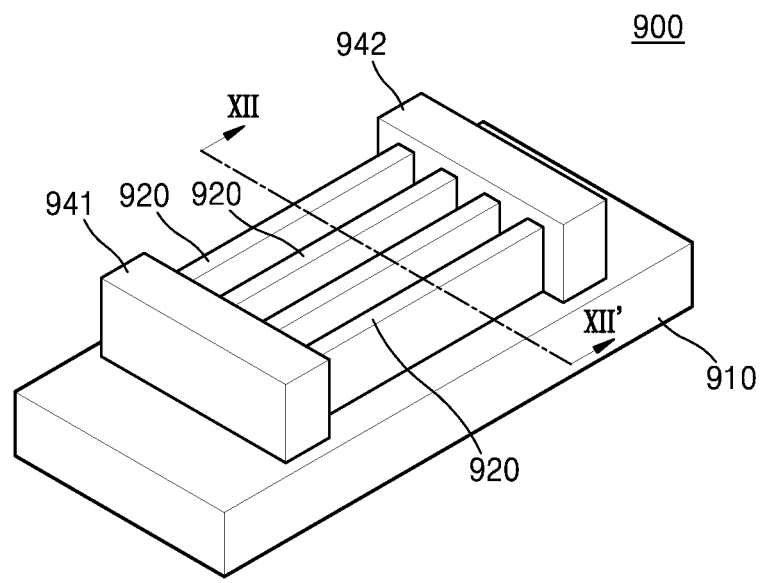
FIG. 11 is a perspective view of a gas sensor according to example embodiments.
Figure 12:
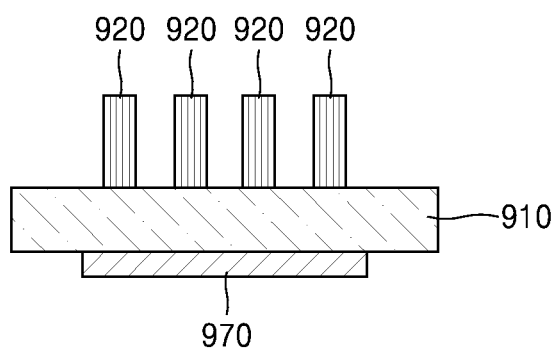
FIG. 12 is a cross-sectional view taken along a line XII-XII' of FIG. 11.

FIG. 11 is a perspective view of a gas sensor 900 according to example embodiments. FIG. 12 is a cross-sectional view taken along a line XII-XII' of FIG. 11.

Referring to FIGS. 11 and 12, the gas sensor 900 may include a substrate 910, a plurality of 2D materials 920 provided on the substrate 910, and first and second electrodes 941 and 942 provided on opposite ends of the 2D materials 920. A heater 970 for heating the 2D materials 920 to a desired (and/or alternatively predetermined) temperature may be further provided on the substrate 910.

The 2D materials 920 are provided on the substrate 910. The 2D materials 920 may be arranged spaced apart from each other with a desired (and/or alternatively predetermined) interval. Alternatively, although FIG. 11 illustrates a case in which the 2D materials 920 are provided on the substrate 910, if necessary, only one 2D material 920 may be provided on the substrate 910.

The 2D materials 920 each denote a semiconductor material having a 2D crystal structure and may have a monolayer or multilayer structure, as described above. Each layer forming the 2D materials 920 may have a thickness of an atomic level. The layers forming the 2D materials 920 may be connected by the Van Der Waals bond.

The 2D materials 920 may include TMD. For example, TMD may include one of metal elements of Mo, W, Nb, V, Ta, Ti, Zr, Hf, Tc, Re, Cu, Ga, In, Sn, Ge, and Pb and one of chalcogen elements of S, Se, and Te. However, the above-described materials are merely a non-limiting example and other materials may be used for TMD. Meanwhile, the 2D materials 920 may be doped with a p-type dopant or an n-type dopant to control mobility. A p-type dopant and an n-type dopant used for graphene or CNT, for example, may be used as the p-type dopant and the n-type dopant. The p-type dopant or the n-type dopant may be doped by an ion implantation method or a chemical doping method.

The 2D materials 920 may have characteristics of adsorbing various types of gases. In example embodiments, each layer forming the 2D materials 920 may be substantially vertically aligned with respect to the substrate 910. Also, the 2D materials 920 may be arranged with a desired (and/or alternatively predetermined) directivity and in parallel to each other. As such, as the 2D materials 920 are substantially vertically aligned with respect to the substrate 910 and the layers are arranged with a desired (and/or alternatively predetermined) directivity and in parallel to each other, surfaces of the 2D materials 920 may have a high reactivity. Accordingly, since various types of gases are efficiently adsorbed, the gas sensor 900 of a high efficiency may be implemented.

First and second electrodes 941 and 941 are provided at opposite ends of the 2D materials 920. When the 2D materials 920 adsorb gases, the electrical characteristics of the 2D materials 920 are changed. The change of the electrical characteristics is measured through the first and second electrodes 941 and 942 and thus whether the gases are adsorbed may be identified.

The heater 970 for heating the 2D materials 920 may be further provided on the substrate 910. The heater 970 may clean the 2D materials 920 that adsorbed gases. In other words, in a state in which the 2D materials 920 adsorb gases, when the heater 970 heats the 2D materials 920 to a desired (and/or alternatively predetermined) temperature, the gases adsorbed by the 2D materials 920 may be removed from the 2D materials. The 2D materials 920 from which the gases are removed may be reused. Alternatively, although FIG. 12 illustrates that the heater 970 is provided on a lower surface of the substrate 910, the present disclose is not limited thereto and the position of the heater 970 may be variously changed. Also, the shape of the heater 970 provided on the substrate 910 may be variously changed.

As described above, in the gas sensor 900, since the 2D materials 920 are vertically aligned on the substrate 910 and the layers forming the 2D materials 920 are formed with a desired (and/or alternatively predetermined) directivity and in parallel to each other, various types of gases may be detected with a high efficiency.

According to example embodiments, the 2D material used as a channel material is vertically aligned with respect to the substrate and the layers forming the 2D material are formed with a desired (and/or alternatively predetermined) directivity and in parallel to each other, a transistor of a fine size with superior performance, for example, a FinFET having a channel width of about 10 nm or less, may be implemented. Also, a gas sensor capable of detecting various types of gases with a high efficiency may be implemented.

Figure 13:
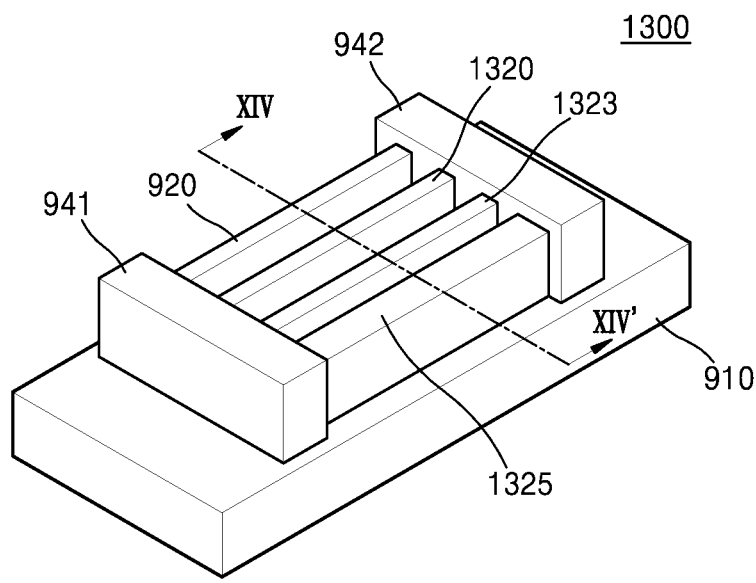
FIG. 13 is a perspective view of a gas sensor according to example embodiments.
Figure 14:
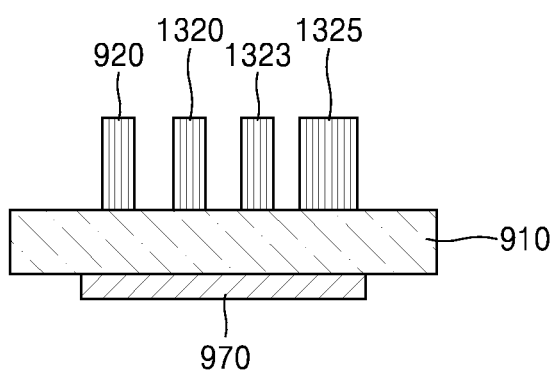
FIG. 14 is a cross-sectional view taken along a line XIV-XIV' of FIG. 13.

FIG. 13 is a perspective view of a gas sensor according to example embodiments. FIG. 14 is a cross-sectional view taken along a line XIV-XIV' of FIG. 13.

According to example embodiments, the gas sensor 1300 illustrated in FIGS. 13-14 may be the same as the gas sensor 900 in FIGS. 9-10 described above, except for the following differences.

Unlike the gas sensor 900 described in FIGS. 11-12, which includes a plurality of 2D materials 920 of a same type that are spaced apart from each other between the first and second electrodes 941 and 942, the gas sensor 1300 may include different types of 2D materials 920 between the first and second electrodes 941 and 942.

For example, as shown in FIGS. 13-14, the gas sensor 1300 may include at least two different 2D materials between the first and second electrodes 941 and 942. The gas sensor 1300 may include the 2D materials 920, 1320, 1323, and 1325 spaced apart from each other between the first and second electrodes 941 and 942.

The 2D material 920 may have a different composition than the 2D material 1320. For example, the 2D material 920 may include one of metal elements of Mo, W, Nb, V, Ta, Ti, Zr, Hf, Tc, Re, Cu, Ga, In, Sn, Ge, and Pb and one of chalcogen elements of S, Se, and Te. The 2D material 1320 may include one of metal elements of Mo, W, Nb, V, Ta, Ti, Zr, Hf, Tc, Re, Cu, Ga, In, Sn, Ge, and Pb and one of chalcogen elements of S, Se, and Te. However, the metal element and/or the chalcogen element in the 2D material 1320 may be different than the metal element and/or the chalcogen element in the 2D material 920. Also, or in the alternative, the 2D materials 1320 and 1325 may have the same composition, but the 2D material 1320 may be doped differently than the 2D material 1323. Also, or in the alternative, the 2D materials 1320 and 1325 may have the same composition, but the 2D material 1325 may have more layers than the 2D material 1320.

FIGS. 15A to 15D illustrate part of a method of manufacturing a transistor according to example embodiments.

Figure 15A:
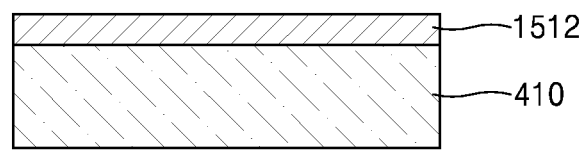
FIGS. 15A to 15D illustrate part of a method of manufacturing a transistor according to example embodiments.
Figure 15B:
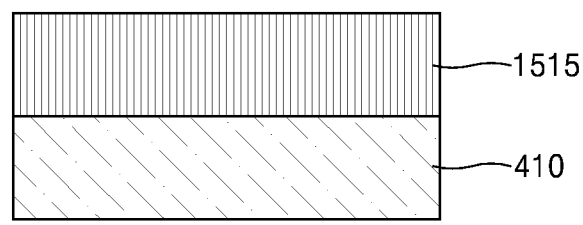
Figure 15C:
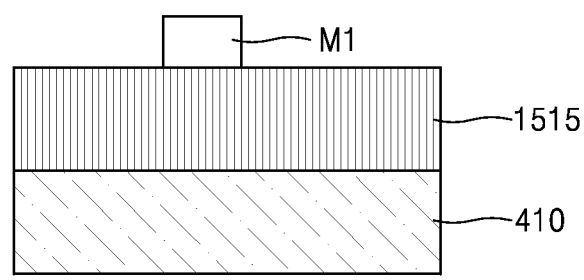
Figure 15D:
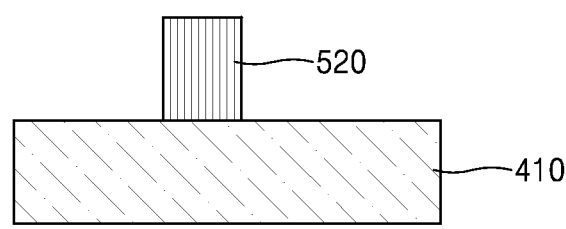

Referring to FIGS. 15A and 15B, a transition metal layer 512 may be formed on a substrate 410. Then a preliminary 2D material 1515 may be grown from the transitional metal layer 512. The preliminary 2D material 1515 may cover an entire surface of the substrate 410. Then, as shown in FIGS. 5C and 5D, the preliminary 2D material 1515 may be patterned by etching a portion of the preliminary 2D material 1515 that is exposed by a mask M1 to form the 2D material 520. After FIG. 15D, the 2D material 520 may be processed according to the operations described with reference to FIGS. 7B and 7C.

It should be understood that example embodiments described herein should be considered in a descriptive sense only and not for purposes of limitation. Descriptions of features or aspects within each device or method according to example embodiments should typically be considered as available for other similar features or aspects in other devices or methods according to example embodiments. While some example embodiments have been particularly shown and described, it will be understood by one of ordinary skill in the art that variations in form and detail may be made therein without departing from the spirit and scope of the claims.

What is claimed is:

1. A transistor comprising:
   a substrate;
   a two-dimensional material on the substrate, the two-dimensional material including at least one layer that is substantially vertically aligned to the substrate such that an edge of the at least one layer is on the substrate and the at least one layer extends substantially vertical to the substrate, each layer being a transition metal dichalcogenide monolayer;
   a source electrode and a drain electrode connected to opposite ends of the two-dimensional material;
   a gate insulation layer on the two-dimensional material between the source electrode and the drain electrode; and
   a gate electrode on the gate insulation layer.

2. The transistor of claim 1, wherein
   the two-dimensional material includes a plurality of layers that are substantially vertically aligned to the substrate, and
   the plurality of layers are parallel to each other.

3. The transistor of claim 1, wherein
   the two-dimensional material includes an upper surface and side surfaces,
   the gate insulation layer and the gate electrode are on the upper surface and the side surfaces of the two-dimensional material.

4. A gas sensor comprising:
a substrate;
at least one two-dimensional material capable of adsorbing a desired gas,
the two-dimensional material including at least one layer that is substantially vertically aligned on the substrate such that an edge of the at least one layer is on the substrate and the at least one layer extends substantially vertical to the substrate,
each layer being a transition metal dichalcogenide monolayer; and
first and second electrodes connected to opposite ends of the two-dimensional material.

5. The gas sensor of claim 4, further comprising:
a heater contacting the substrate, wherein
the heater is configured to remove the desired gas from being adsorbed onto the two-dimensional material by heating the at least one two-dimensional material.

6. The gas sensor of claim 4, wherein
the at least one two-dimensional material includes a plurality of layers that are substantially vertically aligned to the substrate, and
the plurality of layers are parallel to each other.

7. A device comprising:
a substrate;
a two-dimensional material on the substrate, the two-dimensional material including at least one layer that has a width greater than a thickness and is arranged so the width of the at least one layer extends substantially vertical to the substrate, each layer being a transition metal dichalcogenide monolayer, a first electrode and a second electrode spaced apart from each other on the substrate, the first and second electrodes being connected to opposite ends of the two-dimensional material.

8. The device of claim 7, further comprising:
a gate insulation layer on the two-dimensional material between the first electrode and the second electrode; and
a gate electrode on the gate insulation layer, wherein
the gate electrode is spaced apart from the first electrode and the second electrode.

9. The device of claim 7, further comprising:
a heater connected to the substrate, wherein
the two-dimensional material is over the heater,
a gas is capable of adsorbing to the two-dimensional layer, and
the heater is configured to remove the gas from being adsorbed onto the two-dimensional material by heating the two-dimensional material.

10. The device of claim 7, wherein
the two-dimensional material includes a plurality of layers that are substantially vertically aligned to the substrate, and
the plurality of layers are parallel to each other.

* * * * *